United States Patent [19]
Sastry et al.

[11] Patent Number: 6,150,497
[45] Date of Patent: Nov. 21, 2000

[54] METHOD FOR THE PRODUCTION OF POLYGLYCOLIC ACID

[75] Inventors: Bommakanti Bala Subrahmanya Sastry, Branford, Conn.; Andrew Murray Lichkus, York, Pa.

[73] Assignee: Sherwood Services AG, Schaffhavsen, Switzerland

[21] Appl. No.: 09/229,810

[22] Filed: Jan. 13, 1999

Related U.S. Application Data

[60] Provisional application No. 60/071,489, Jan. 14, 1998.

[51] Int. Cl.[7] .................................................. C08G 63/68
[52] U.S. Cl. ........................... 528/354; 528/272; 528/361
[58] Field of Search ...................................... 528/354, 361, 528/272

[56] References Cited

U.S. PATENT DOCUMENTS

| | | | |
|---|---|---|---|
| 4,095,600 | 6/1978 | Casey et al. | 128/335.5 |
| 4,650,851 | 3/1987 | Rhum et al. | 528/354 |

*Primary Examiner*—Terressa M. Boykin

[57] ABSTRACT

A method for the production of polyglycolic acid polymer useful in the manufacture of sutures, meshes, gauzes, molded clips and like medical articles.

1 Claim, No Drawings

METHOD FOR THE PRODUCTION OF POLYGLYCOLIC ACID

This application claims the benefit of U.S. Provisional No. 60/071,489 filed Jan. 14, 1998.

FIELD OF THE INVENTION

The present invention relates to a novel method for the production of polyglycolic acid polymer useful in the manufacture of medically useful materials such as sutures, meshes, gauzes, molded clips and the like, and more particularly, to a method of producing colored or natural polyglycolic acid polymer with inherent viscosity values over 1.10 dl per gram for use in manufacturing surgical sutures and the like.

BACKGROUND OF THE INVENTION

Polyglycolic acid polymers are known in the art and described in U.S. Pat. Nos. 3,468,853 and 3,875,937 incorporated herein by reference. Such polymers are solid, highly bioabsorbable and highly hydrolyzable. Polyglycolic acid polymers due to their ease of polymerization and other desirable characteristics are commonly spun, braided or otherwise processed into woven or nonwoven fabrics useful as surgical materials such as surgical sutures or gauze, or molded into medically useful devices such as clips or staples. High molecular weight, i.e., approximately 100,000 molecular weight or above, polyglycolic acid materials are naturally beige in color. When spun for use as sutures, the natural or beige polyglycolic acid sutures upon use become stained red with blood. The blood stained suture stitches are hardly distinguishable in tissue which can present difficulties during surgery.

In order to solve this surgical suture visibility problem, absorbable polymers are commonly colored with dyes or pigments so as to permit their distinction at first glance when in tissue, even after stained with blood. A coloring agent or pigment employed to color sutures made of an absorbable high molecular weight material such as polyglycolic acid must be nontoxic to human bodies and be absorbed by tissue and excreted. Currently, surgical sutures dyed violet, green or blue are available commercially to address this surgical suture visibility issue.

In attempting to produce polyglycolic acid suitable for the manufacture of bioabsorbable sutures, it was discovered that the customary method known in the art for producing the same in a size 65, i.e., 65 gallon, conical vortex reactor was unexpectedly unsuccessful upon changing the process over to a size 10, i.e., 10 gallon, conical vortex reactor. The customary method, typically carried out in essentially five steps, failed to produce a useful polymer. A summary of the five step process proven unsuccessful in producing useful polymer in the size 10 conical vortex reactor includes 1) distilling fresh liquid glycolide into a collection vessel maintained at 95 degrees Celsius and then charging the same into a size 65 conical vortex reactor, preheated to a temperature of 130 degrees Celsius, until half filled, 2) adding catalyst and initiator, 3) filling the remaining unfilled half of the reactor with glycolide, 4) heating the reactor until the glycolide reaches a uniform temperature of 135 degrees Celsius, and 5) increasing the reactor temperature at one degree Celsius intervals, i.e., "ramping", until the "glycolide" reaches a uniform temperature of 220 degrees Celsius.

As described above, the conventional, known process for producing polyglycolic acid polymer in a size 65 conical vortex reactor is unsatisfactory for producing the same polymer using a size 10 conical vortex reactor.

SUMMARY OF THE INVENTION

An object of this invention is to provide a process for producing polyglycolic acid using a size 10 or smaller conical vortex reactor suitable for medical use. Due to the aforementioned manufacturing problem, the present inventors carried out an investigation in order to develop a method of producing the desired sutures using a size 10 or smaller conical vortex reactor. As a result, it has now been discovered that the key to producing useful polyglycolic acid polymer is to ensure that the manufacturing process has adequate holding times at specific temperatures to allow for complete polymerization. By changing from a size 65 conical vortex reactor to a smaller size 10 reactor, it was found that the known temperatures useful for producing polymer in accordance with the prior art five step process were reached too rapidly and adequate time for complete polymerization was lacking. In addition to the development of an unique manufacturing process for the production of polyglycolic acid using a size 10 or smaller conical vortex reactor, it was discovered that sutures formed from the polymer made by the subject unique process have higher strength, higher inherent viscosity, i.e., 1.10 dl per gram or greater, improved consistency, overall superior quality and are more economical to produce due to less wasted product based on the smaller reactor size.

DETAILED DESCRIPTION OF THE INVENTION

It is important to note in the interest of clarity, that throughout the process of the present invention glycolide, the starting material, is gradually polymerized into the end or final product, polyglycolic acid. During this polymerization process, the ratio of glycolide to polyglycolic acid present in the reaction vessel gradually diminishes. Although throughout the majority of this polymerization process both glycolide and polyglycolic acid polymer are present, for the sake of simplicity, the same will be referred to as "glycolide" up to the point of completion of the polymerization process.

The unique process of the present invention for the preparation of polyglycolic acid (PGA) is initiated by preheating a size 10 conical vortex reactor to approximately 140 degrees Celsius. Solid glycolide, approximately 80 pounds due to the size of the reactor, is placed in a melter and melted to achieve a uniform molten glycolide temperature of approximately 120 degrees Celsius. It is critical to the subject process that the molten glycolide temperature uniformly reaches and is maintained at a temperature between approximately 115 to 125 degrees Celsius, but preferably approximately 120 degrees Celsius. At a temperature of approximately 120 degrees Celsius, the molten glycolide will attain in approximately 95 to 120 minutes its more stable and preferred beta form. In this preferred beta form, the molten glycolide has a clear appearance. If the molten glycolide temperature is lower than approximately 115 degrees Celsius, the polymerization reaction does not reach completion. If the glycolide temperature is higher than approximately 125 degrees Celsius or remains at approximately 125 degrees Celsius for a long period of time, such as for approximately twenty to thirty minutes or more, the glycolide ring is broken thus forming glycolic acid as evidenced by an acid content determination. Glycolic acid is undesirable for the present use due to its ability to act as an initiator or a catalyst resulting in a Lower molecular weight polymer. Accordingly, once the glycolide is completely melted and reaches a uniform temperature of approximately 120 degrees Celsius, an initiator, such as but not limited to lauryl alcohol or diethylene glycol, and a catalyst, such as but not limited to stannous chloride dihydrate or stannous octoate, are added to the molten glycolide in the melter. Preferably, 0.01 to 0.04 mole percent of lauryl alcohol initiator, or approximately 0.2 to 0.8 ml lauryl alcohol/kg glycolide or more preferably approximately 0.6 ml lauryl alcohol/kg glycolide of initiator is added to the melter. As for the catalyst, preferably 0.0005 to 0.028 g stannous chloride dihydrate/kg glycolide or more preferably approximately 0.026 g stannous chloride dihydrate/kg glycolide of catalyst is likewise added to the melter. The contents of the melter are then charged to the preheated reactor and blended. The temperature of the reactor is then adjusted in one step to approximately 160 degrees Celsius and held for approximately 15 to 20 minutes, but preferably approximately 18 minutes until the glycolide reaches a uniform temperature of approximately 155 to 165 degrees Celsius, but preferably 160 degrees Celsius.

It is important to note that in the subject method the temperatures and holding times specified are critical to the success of the process. If the molten glycolide is held at the specified temperatures for too long, the polymer chains will not continue to build throughout the process and a low molecular weight polymer will result. If the molten glycolide is not held at the specified temperatures for a sufficient amount of time, polymerization will not reach completion. Ensuring that the molten glycolide reaches the particular temperatures specified is likewise critical to the success of the process as already noted above.

After the glycolide reaches the desired temperature of approximately 160 degrees Celsius, it is held at this temperature for approximately 10 to 15 minutes but preferably 13 minutes to allow for complete polymerization. The temperature of the reactor is then adjusted to approximately 180 degrees Celsius and held for approximately 10 to 15 minutes, but preferably approximately 13 minutes until the glycolide reaches a uniform temperature of approximately 175 to 185 degrees Celsius, but preferably approximately 180 degrees Celsius. The glycolide is then held at approximately 180 degrees Celsius for approximately 3 to 8 minutes, but preferably approximately 5 minutes. The temperature of the reactor is then adjusted in one step to approximately 190 degrees Celsius and held for approximately 5 to 10 minutes, but preferably approximately 8 minutes until the glycolide reaches a uniform temperature of approximately 185 to 195 degrees Celsius, but preferably approximately 190 degrees Celsius. The glycolide is then held at this temperature for approximately 3 to 8 minutes, but preferably 5 minutes. The temperature of the reactor is then adjusted in one step to approximately 205 to 235 degrees Celsius, but preferably approximately 220 degrees Celsius and held until the glycolide maximum viscosity peak is reached which takes approximately 20 to 25 minutes.

The glycolide maximum viscosity peak is reached at the point when resistance to the reactor's internal blending mechanism stops its gradual increase throughout the subject process and reaches a plateau.

The subject method which includes increasing the temperature of the glycolide in approximately 10 to 40 degree Celsius increments followed by approximately 5 to 40 minute "hold" periods is coined "stepping".

Once the molten glycolide reaches a uniform temperature of approximately 220 degrees Celsius, a vacuum of approximately 40 to 90 mm Hg, but preferably approximately 50 mm Hg is applied for approximately 10 to 20 minutes, but preferably approximately 15 minutes to effectively remove residual monomer from the system. If the vacuum is too low, the residual unreacted monomer will not be removed from the system. Additionally, it has been discovered that the removal of residual monomer from this process improves the in vitro strength of the final suture product. If the vacuum is too high, polymer bonds may be broken resulting in a low molecular weight product.

Dye or pigment such as D&C Violet No. 2, identified as 1-hydroxy-4-((4-methylphenyl)amino)-9,10-anthracenedione, D&C Green No. 6, identified as 1,4-bis ((4-methylphenyl)amino)-9,10-anthracenedione, D&C Blue No. 6, identified as (Delta 2,2'-biindoline)-3,3'-dione, or the like as described in the handbook of U.S. Colorants for Food, Drugs and Cosmetics by Daniel M. Marrion (1979), is then optionally added to the polymer. The dye or pigment may be added to the polymer at approximately 0.16 to 0.24 weight percent but preferably approximately 0.22 percent by weight to achieve approximately 0.18 percent by weight dye in the final product for adequate color. However, depending on the shade or intensity of color desired in the final product, the amount of dye or pigment added to the polymer may be adjusted accordingly. After the dye or pigment is added, the polymer is blended for approximately 3 to 8 minutes, but preferably approximately 5 minutes for uniform coloration throughout the polymer batch.

The final polyglycolic acid polymer produced in accordance with the present invention has an inherent viscosity of at least approximately 1.10 dl/g but preferably, within the range of approximately 1.10 to 1.50 dl/g, or more preferably, within the range of approximately 1.10 to 1.40 dl/g to achieve sutures having desirable commercial characteristics. The inherent viscosity values of the polymer produced in accordance with the subject method were determined in a solvent system of hexa fluoro acetone sesquihydrate (HFAS) at a temperature of 30 degrees Celsius.

The subject process for the production of polyglycolic acid polymer in a size 10 conical vortex reactor has been found to be useful for the production of polymer in reactors of varying size, such as a size 4 conical vortex reactor as described in Example 2 below. It is also believed that the stepping process of the present invention would likewise produce suitable polymer in reactors of larger size, such as a 65 conical vortex reactor, as well as the smaller sizes already noted.

The polyglycolic acid polymer produced it accordance with the subject method is suitable for use in manufacturing useful fibrous medical materials such as sutures, gauzes, meshes and the like. To manufacture such fibrous medical materials using the subject polymer, the polymer is processed into filament bundles and braids in a manner known to those skilled in the art or similar to that described in Examples 2 through 4 of U.S. Pat. No. 3,839,297 incorporated herein in its entirety by reference. When spinning or extruding the preferably colored polymer produced by the subject process for use in the manufacture of surgical sutures and the like, the colored polymer is melt-spun through a spinneret having 3 to 300, but preferably 3 to 75, or more preferably 8 to 56, fine holes for greater manageability. The polymer is melt-spun through the spinneret by means of a melt extruder so as to produce filament bundles which are twisted and/or braided in a manner known to those skilled in the art. Such extrusion is conducted at approximately 240 to 290 degrees Celsius and at an extrusion pressure of approximately 1000 to 3500 psi but preferably approximately 3000 psi produced through the use of an extrusion screw.

After melt-spinning, the polyglycolic acid filament bundles are drawn by first passing it over a roll heated to approximately 55 to 65 degrees Celsius, but preferably 60 degrees Celsius. The bundles are then drawn over a second roll heated to approximately 105 to 115 degrees Celsius, but preferably 110 degrees Celsius. The second roll is set to rotate at a speed of approximately four and one half times the speed of the first roll. The drawn filament bundles are then ready for braiding and/or twisting into multifilament fibers. Once braided or twisted in accordance with methods known in the art, the subject multifilament fibers have a mean tensile strength of at least 90,000 psi. More specifically, the fibers have a mean tensile strength of approximately 105,000 to 115,000 psi, but more preferably approximately 109,400 psi for a size 0/1 braid, approximately 135,000 to 150,000 psi, but more preferably approximately 142,100 psi for a size 4-0 braid, and approximately 90,000 to 100,000 psi, but preferably approximately 95,000 psi for a size 7-0 braid. The same sutures when tested have a hydrolytic strength after seven hours in a buffer of 6.1 pH maintained at approximately 80 degrees Celsius of at least 35,000 psi. More specifically, the sutures have a hydrolytic strength of approximately 38,800 psi for a braid of size 0/1, approximately 36,400 psi for a braid of size 4-0, and approximately 36,800 psi for a braid of size 7-0. After braiding or twisting the multifilaments fibers as noted above, the fiber sutures or medical material fibers are packaged and sterilized in accordance with methods known in the art for use as surgical sutures or similar medical materials such as meshes or gauze.

The method of the present invention is described in still further detail in the following examples which are not intended to be limiting thereto.

EXAMPLE 1

PROCESS TO PRODUCE POLYGLYCOLIC ACID

Fifty (50) pounds of distilled crystalline glycolide was charged into a melter and thirty (30) pounds of distilled crystalline glycolide was charged into another melter. The glycolide in these melters were completely melted in one and a half to two hours by carefully controlling the temperature between 115 degrees and 125 degrees Celsius. To the completely molten glycolide was then added 0.94 g of stannous chloride dihydrate dissolved in 21.80 ml of lauryl alcohol. The entire quantity of glycolide was then released into the reactor which was preheated to 140 degrees Celsius. The glycolide in the reactor was stirred at a rate of 36 revolutions per minute. The temperature of the reactor was immediately adjusted to 160 degrees Celsius. It took approximately 18 minutes for the reactor to attain 160 degrees Celsius. The reactor was then held at 160 degrees Celsius for 13 minutes. The temperature of the reactor was then set to 180 degrees Celsius and was held for approximately 13 minutes until the glycolide reached a uniform temperature of 180 degrees Celsius. The glycolide was then held at 180 degrees Celsius for 5 minutes. The temperature of the reactor was then adjusted to 190 degrees Celsius and was held for approximately 8 minutes until the glycolide reached a uniform temperature of 190 degrees Celsius. The glycolide was then held at 190 degrees Celsius for 5 minutes. The reactor temperature was then set of 220 degrees Celsius and was held at 220 degrees Celsius for 20 to 25 minutes until the peak power drain on the reactor stirrer is attained, i.e., maximum viscosity. A vacuum of 50 mm Hg was then applied for 15 minutes. Stirring was then stopped and 80 g of D&C Violet No. 2 was charged to the reactor. The colorant was blended with the polymer for 5 minutes and the violet colored polyglycolic acid polymer was then discharged from the reactor. The polymer was discharged on to a conveyor belt and was pelletized immediately. The inherent viscosity of the resulting polymer was 1.24 measured on a Cannon-Fenske style viscometer. The following measurements were obtained upon testing braid produced from polymer made in accordance with the subject process. The braid measurements listed below were taken as the result of tests conducted in accordance with the method described in the current United States Pharmacopoeia. These test results showed the tensile strength of the subject sutures to be at least 90,000 psi and the hydrolytic strength to be at least 35,000 psi, in addition to the more specific results which follow.

Tensile Strength 109,400 psi (mean) for a braid size 0/1

142,100 psi (mean) for a braid size 4-0

95,000 psi (mean) for a braid size 7-0

Hydrolytic Strength 38,800 psi after seven hours in a buffer of 6.1 pH at 80 degrees Celsius for a braid size 0/1

36,400 psi after seven hours in a buffer of 6.1 pH at 80 degrees Celsius for a braid size 4-0

36,800 psi after seven hours in a buffer of 6.1 pH at 80 degrees Celsius for a braid size 7-0

EXAMPLE 2

PROCESS TO PRODUCE POLYGLYCOLIC ACID

Two (2) pounds of distilled glycolide was charged in to a 2 liter volumetric flask and two (2) additional pounds of distilled glycolide into another flask. The flasks were stoppered and were placed in two separate hot heating mantles. The flasks were heated with heat guns until all the crystalline glycolide was melted. When the temperature of the molten glycolide attained 120 degrees Celsius, 0.052 g of stannous chloride dihydrate and 1.2 ml of lauryl alcohol were stirred into the molten glycolide and transferred into a size 4 conical vortex reactor preheated to 140 degrees Celsius. The temperature of the reactor was immediately raised to 160 degrees Celsius. It took approximately 13 minutes to reach 160 degrees Celsius. The reactor was held at 160 degrees Celsius for 10 minutes and was then raised to 180 degrees Celsius. It took approximately 13 minutes to reach 180 degrees Celsius. The reactor was held at 180 degrees Celsius for 5 minutes. The temperature of the reactor was then raised to 190 degrees Celsius. It took approximately 8 minutes to reach 190 degrees Celsius. The reactor was held at this temperature for 5 minutes. The reactor temperature was then adjusted to 220 degrees Celsius. It took approximately 22 minutes to reach 220 degrees Celsius. The reactor was held at 220 degrees Celsius until the viscosity of the polymer reached a maximum and stabilized. At this stage, a vacuum of 50 mm Hg was applied for 15 minutes. The vacuum was released and 4.4 grams of D&C Violet No. 2 dye was charged to the reactor. The dye was blended with the polymer for 5 minutes and the polymer was then discharged from the reactor. The inherent viscosity of the resulting polymer was 1.28 measured on a Cannon-Fenske style viscometer. Sutures manufactured from the resultant polymer were found to have the following characteristics when tested in accordance with test methods set forth in the current United States Pharmacopoeia.

IN VIVO STRENGTH OF 4/0 SUTURE

DAY 0 134,080 psi 100%

DAY 14 109,740 psi 81.8%

DAY 21 95,930 psi 71.6%

For purposes of comparison, the same test was conducted using a suture produced using the prior art method of production. The results of the test are listed below.

IN VIVO STRENGTH OF PRIOR ART 4/0 SUTURE

DAY 0 128,310 psi 100%

DAY 14 89,492 psi 69.6%

DAY 21 48,378 psi 37.6%

The above data illustrates the subject suture's increased in vivo strength, achieved through the use of polymer manufactured in accordance with the present process.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

What is claimed is:

1. A method for the production of polyglycolic acid polymer useful in the manufacture of surgical sutures and like medical materials comprising:

a.) adding initiator and catalyst to 115 to 125 degree Celsius molten glycolide and blending;

b.) increasing the glycolide temperature to approximately 160 degrees Celsius and holding for approximately 13 minutes;

c.) increasing the glycolide temperature to approximately 180 degrees Celsius and holding for approximately 5 minutes;

d.) increasing the glycolide temperature to approximately 190 degrees Celsius and holding for approximately 5 minutes; and e.) increasing the glycolide temperature to approximately 220 degrees Celsius and applying a vacuum for approximately 15 minutes to form polyglycolic acid.

* * * * *